United States Patent
Sandler et al.

[11] Patent Number: 5,741,934
[45] Date of Patent: Apr. 21, 1998

[54] PREPARATION OF PRIMARY MERCAPTANS

[76] Inventors: Stanley R. Sandler, 221 Hemlock La., Springifeld, Del. 19064; Pamela J. Peerce-Landers, 550 Sanatoga Rd., Sanatoga, Pa. 19464; Christian Forquy, 7 rue Jean Sarrailh, 64360 Monein, France

[21] Appl. No.: 629,823

[22] Filed: Apr. 10, 1996

[51] Int. Cl.⁶ .................................................. C07C 319/00
[52] U.S. Cl. .................................................. 568/73
[58] Field of Search .................................................. 568/73

[56] References Cited

U.S. PATENT DOCUMENTS

| | | | |
|---|---|---|---|
| 2,443,852 | 6/1948 | Eaton et al. | 568/73 |
| 2,468,739 | 5/1949 | Eaton et al. | 568/73 |
| 2,498,872 | 2/1950 | Bell et al. | 568/73 |
| 2,531,601 | 11/1950 | Bell et al. | 568/73 |
| 2,592,089 | 4/1952 | Weimer | 568/73 |
| 4,612,398 | 9/1986 | Lee | 568/73 |

OTHER PUBLICATIONS

"A Remarkably Efficient Initiation by 9–BBN in the Radical Addition Reactions of Alkanethiols to Alk–1–enes" Masuda et. al., J. Chem. Soc., Chem. Commun., 1991, pp. 1444–1445.

*Primary Examiner*—Paul J. Killos
*Attorney, Agent, or Firm*—Gilbert W. Rudman; Stanley A. Marcus

[57] ABSTRACT

A process is disclosed for the preparation of primary mercaptans by reacting hydrogen sulfide with an alpha-olefin in the presence of a reaction initiating amount of a borane represented by the formula $R_2BH$ or $R_3B$ where R is a linear or cyclic aliphatic or aryl group.

10 Claims, No Drawings

PREPARATION OF PRIMARY MERCAPTANS

BACKGROUND OF THE INVENTION

This invention relates to the preparation of mercaptan products having a high proportion of primary mercaptans by a facile, low temperature reaction of hydrogen sulfide with an alpha ($\alpha$)-olefin. More particularly, it relates to the preparation of predominantly $C_2$–$C_{20}$ primary alkyl mercaptans by the reaction of hydrogen sulfide with a $C_2$–$C_{20}$ $\alpha$-olefin in the presence of a reaction initiating amount of a borane represented by the formula $R_2BH$ or $R_3B$ where R is a linear or cyclic aliphatic or aryl group.

PRIOR ART

A commercial process for the preparation of primary mercaptans involves ultraviolet light activation of hydrogen sulfide to add to $\alpha$-olefins at a temperature of about 40° C. This process requires costly capital equipment and produces undesirably large amounts of waste by-products, i.e., 2-mercaptans and sulfides.

An article authored by Y. Masuda et al. describes the use of 9-BEN (9-borabicyclo [3.3.1] nonane) to initiate the radical addition of alkanethiols to alkenes under very mild conditions to provide the corresponding dialkylsulfides (see J. Chem. Soc., Chem. Comm., 1444 (1991); "A remarkably Efficient Initiation by 9-BBN in the Radical Addition Reactions of Alkanethiols to Alk-1-enes").

STATEMENT OF THE INVENTION

This invention is a process for the preparation of a mercaptan product having a high proportion of primary mercaptans comprising reacting hydrogen sulfide with a $C_2$–$C_{20}$ $\alpha$-olefin in the presence of a reaction initiating amount of a borane represented by the formula $R_2BH$ or $R_3B$ where R is a linear or cyclic aliphatic, or aryl group, and recovering a mercaptan product.

DETAILED DESCRIPTION OF THE INVENTION

This invention is a facile, low temperature process for the manufacture of predominantly primary $C_2$–$C_{20}$ alkyl mercaptans where hydrogen sulfide ($H_2S$) is reacted with a $C_2$–$C_{20}$ $\alpha$-olefin in the presence of a reaction initiating amount of a borane represented by the formula $R_2BH$ or $R_3B$ where R is a linear or cyclic aliphatic or aryl group.

The $C_2$–$C_{20}$ $\alpha$-olefins useful for this invention include, for example, ethylene, 1-propene, 1-butene, 1-hexene, 1-octene, 1-decene, 1-dodecene, 1-octadecene and 1-eicosene.

The reaction of the process is represented by the following equation:

The temperature at which this reaction is carried out preferably ranges between about −20° and about 100° C., more preferably between 0° and 25° C. The reaction pressure preferably ranges from about 200 to about 2000 psig, more preferably between about 200 and about 500 psig. The reaction time preferably ranges from about 0.25 to about 5 hours, more preferably from about 1 to 3 hours. The preferred mole ratio of the $H_2S$ to the $\alpha$-olefin in the reaction is about 4 to 30:1, more preferably 7 to 20:1. The preferred mole ratio of the borane initiation to the $\alpha$-olefin is about 0.001 to 0.010:1, more preferably 0.004 to 0.007:1.

The borane initiator has one of the following formulas:

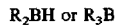

where R is the same or different linear or cyclic $C_1$–$C_{20}$, preferably $C_1$–$C_4$ aliphatic group, or $C_6$–$C_{12}$ aryl group where each of $R_2$ and $R_3$ may be a part of the cyclic or aromatic structure. Examples of these borane initiators include 9-BBN (9-borabicyclo [3.3.1] nonane), beta-hexyl-9-BBN, beta-allyl-9-BBN, beta-methoxy-9-BBN, dioctylborane, dioctadecylborane, diphenyl borane, triethyl borane, triisobutyl borane, dipropylphenyl borane and the like. Mixtures of these boranes, in any proportion, may be employed to initiate the reaction. The borane initiators may be used neat or in a carrier solvent, e.g., tetrahydrofuran, dimethyl sulfide, dioxane and the like. For most reactions of this invention, a solvent is not needed.

The benefits of this invention are that the process is generally carried out at low temperature which reduces the formation of waste by-product secondary mercaptans and sulfides. Further, the ratio of secondary/primary mercaptans is reduced to obtain higher yields of the target primary mercaptan products.

The following examples are set forth to demonstrate the process of this invention.

EXAMPLES 1–6

GENERAL PROCEDURE

Hydrogen sulfide was added to an evacuated and cooled (−30° C.) 100 cc Parr Autoclave by gravity transfer from a cylinder (in the case of Example 1, 38.6 g of hydrogen sulfide was added). Then 1-octene with the borane initiator dissolved in it [in the case of Example 1, 17.14 g (0.153 moles) of 1-octene and 1.074 g 9-BBN (0.000765 mole)] was added to the autoclave reactor by vacuum transfer (without air). The autoclave reactor was stirred and warmed to the temperature of the reaction as noted for each example shown in Table I below. Periodically, samples were removed from the reactor via vacuum transfer from a sampling valve to a weighed cylinder. Hexane was added to the sample cylinder and the cylinder contents warmed to room temperature. The sample was then removed under a hood for gas chromatographic analysis (GC). The reaction conditions and GC analysis results are shown in Tables I & II, following:

TABLE 1

| | Reaction Conditions | | | | |
|---|---|---|---|---|---|
| Example No. | Initiator | Mole Ratio $H_2S$/1-Octane | Temp °C. | Time Hrs. | Mole Ratio Initiator/1-Octene |
| 1 | 9-BBN | 7.4 | 27° | 3 | 0.005 |
| 2 | 9-BBN | 7.4 | 40° | 1 | 0.005 |
| 3 | 9-BBN | 8.5 | 27° | 3 | 0.0047 |
| 4 | 9-BBN | 8.5 | 40° | 1 | 0.0047 |
| 5 | $(C_2H5)_3B$ | 8.4 | 28–42° | 3 | 0.0049 |
| 6 | 9-BBN | 7.4 | 21–29° | 2 | 0.0045 |

TABLE II

| | | | | | | |
|---|---|---|---|---|---|---|
| | | GC Results | | | | |
| Example No. | 1-Octene wt. % | 1-Octyl Mercaptan wt. % | 2-Octyl Mercaptan wt. % | 2-Ethyl Hexyl Mercaptan wt. % | Sulfides wt. % | Ratio Secondary: Primary Mercaptans |
| 1 | 43.7 | 50.4 | 1.8 | 0.17 | 2.2 | 0.0357 |
| 2 | 37.2 | 55.5 | 2.1 | 0.19 | 3.3 | 0.0378 |
| 3 | 76.8 | 22.5 | 0.8 | 0.08 | 0.8 | 0.0355 |
| 4 | 76.9 | 20.6 | 0.7 | 0.06 | 0.6 | 0.0340 |
| 5 | 81.7 | 16.2 | 0.53 | 0.05 | 0.51 | 0.0327 |
| 6 | 68.5 | 27.6 | 0.71 | 0.04 | 1.5 | 0.0257 |

We claim:

1. A process for the manufacture of mercaptan products containing a high proportion of primary mercaptans comprising reacting hydrogen sulfide with a $C_2$–$C_{20}$ alpha olefin in the presence of a reaction initiating amount of a borane represented by the formulas $R_2BH$ or $R_3B$ where R is a linear, or cyclic aliphatic, or aryl group, and recovering a mercaptan product.

2. The process of claim 1 wherein said alpha olefin is a $C_4$–$C_{10}$ olefin.

3. The process of claim 1 wherein said borane is 9-borabicyclo [3.3.1] nonane.

4. The process of claim 1 wherein the reaction is carried out at a temperature within the range of about −20° to about 100° C. and a pressure of from about 200 to about 2000 psig.

5. The process of claim 4 wherein said reaction is carried out at a hydrogen sulfide to alpha olefin mole ratio within the range of 4 to 30:1, and a borane to alpha olefin mole ratio within the range of 0.001 to 0.01:1.

6. The process of claim 5 wherein the reaction time ranges from about 0.25 to about 5 hours.

7. The process of claim 5 wherein said borane is 9-borabicyclo [3.3.1] nonane.

8. The process of claim 2 wherein said borane is 9-borabicyclo [3.3.1] nonane, and the reaction is carried out at a temperature within the range of about 0° to about 25° C., a pressure between about 200 and about 500 psig, and for a time between about 1 and about 3 hours.

9. The process of claim 8 wherein said reaction is carried out at a hydrogen sulfide to alpha olefin mole ratio within the range of about 7 to 20:1 and at a borane to alpha olefin mole ratio within the range of about 0.004 to 0.007:1.

10. The process of claim 1 wherein said borane is dissolved in an inert organic solvent therefor.

* * * * *